(12) United States Patent
Park

(10) Patent No.: US 11,090,069 B2
(45) Date of Patent: Aug. 17, 2021

(54) PATIENT-SPECIFIC, MECHANICAL SELF-LOCKING, FEMORAL AND TIBIAL SURGICAL CUTTING JIGS

(71) Applicant: Lento Medical Inc., Fremont, CA (US)

(72) Inventor: Ilwhan Park, Walnut Creek, CA (US)

(73) Assignee: Lento Medical, Inc., Houston, TX (US)

( * ) Notice: Subject to any disclaimer, the term of this patent is extended or adjusted under 35 U.S.C. 154(b) by 3 days.

(21) Appl. No.: 16/239,329

(22) Filed: Jan. 3, 2019

(65) Prior Publication Data

US 2019/0239903 A1    Aug. 8, 2019

Related U.S. Application Data

(60) Provisional application No. 62/628,117, filed on Feb. 8, 2018.

(51) Int. Cl.
*A61B 17/17*     (2006.01)
*A61B 34/10*     (2016.01)
(Continued)

(52) U.S. Cl.
CPC ........ *A61B 17/1764* (2013.01); *A61B 17/155* (2013.01); *A61B 17/157* (2013.01);
(Continued)

(58) Field of Classification Search
CPC ... A61B 17/17; A61B 17/1764; A61B 17/154; A61B 17/155; A61B 17/157
See application file for complete search history.

(56) References Cited

U.S. PATENT DOCUMENTS 6,347,240 B1 * 2/2002 Foley .................. A61B 5/0064
600/426
8,160,345 B2 * 4/2012 Pavlovskaia ........... A61B 5/055
382/131
(Continued)

FOREIGN PATENT DOCUMENTS

WO    WO2010063117 A1    6/2010

OTHER PUBLICATIONS

A. Durandet et al., "Radiographic analysis of lower limb axial alignments", Proceedings of the World Congress on Engineering, 2013, vol. II, WCE 2013, Jul. 3-5, 2013 London UK, 6 pages.
(Continued)

*Primary Examiner* — Matthew J Lawson
*Assistant Examiner* — Lisa Nguyen
(74) *Attorney, Agent, or Firm* — Mark Protsik; Thomas Schneck

(57) ABSTRACT

Jigs for guiding femur and tibia resectioning in knee surgery contain bone-jig contact surfaces and a cutting guide as a single unitary piece. Contact surfaces are curvilinear surfaces formed into ends of projections from a jig base. Each jig has three pairs of contact surfaces selected to abut low-wear, lateral and medial, articular surface features, such that only one self-locking position against the bone (or cartilage) is possible and the integral cutting guide will define only one cut plane for the resectioning. An improved rotational transformation that converts scan views into desired proper axes is based on projections of rotated coordinates onto the plane of rotation to produce parameters that closely correspond to the joint surfaces in the desired jig coordinates.

4 Claims, 19 Drawing Sheets

(51) Int. Cl.
   *A61B 17/15*  (2006.01)
   *A61B 17/00*  (2006.01)
(52) U.S. Cl.
   CPC .... *A61B 34/10* (2016.02); *A61B 2017/00526* (2013.01); *A61B 2034/105* (2016.02); *A61B 2034/108* (2016.02)

(56) References Cited

U.S. PATENT DOCUMENTS

| | | | |
|---|---|---|---|
| 8,588,892 | B2 | 11/2013 | Hladio et al. |
| 8,608,749 | B2 | 12/2013 | Meridew et al. |
| 9,339,226 | B2 * | 5/2016 | van der Walt ..... A61B 17/1764 |
| 9,375,588 | B2 * | 6/2016 | Salomir ................ A61N 7/02 |
| 9,649,160 | B2 * | 5/2017 | van der Walt ........ A61F 2/4657 |
| 9,775,725 | B2 | 10/2017 | van der Walt et al. |
| 10,595,941 | B2 * | 3/2020 | Herrmann ............ A61B 34/10 |
| 2007/0276224 | A1 * | 11/2007 | Lang .................... A61B 5/1038 600/410 |
| 2011/0184419 | A1 | 7/2011 | Meridew et al. |
| 2011/0282473 | A1 * | 11/2011 | Pavlovskaia ............ G06F 19/00 700/98 |
| 2013/0150862 | A1 * | 6/2013 | Aram .................. A61B 17/157 606/88 |
| 2014/0115872 | A1 * | 5/2014 | Steines .................. B23P 19/00 29/592 |
| 2014/0148809 | A1 * | 5/2014 | Schmalzried ...... A61B 17/1764 606/80 |
| 2015/0088142 | A1 * | 3/2015 | Gibson .............. A61B 17/1764 606/88 |
| 2015/0182292 | A1 | 7/2015 | Hladio et al. |
| 2019/0223886 | A1 * | 7/2019 | Fritzinger ............ A61B 17/157 |

OTHER PUBLICATIONS

H. Kawakami et al., "Effects of rotation on measurement of lower limb alignment for knee osteotomy", Journal of Orthopaedic Research, 22, 2004, pp. 1248-1253.

R.G. Marx et al., "Reliability of lower extremity alignment measurement using radiographs and PACS", Knee Surg Sports Traumatol Arthrosc, 2011, 19:1693-1698.

G. McDaniel et al., A comparison of five approaches to measurement of anatomic knee alignment from radiographs, NIH Public Access, Author Manuscript, Osteoarthritis Cartilage, Feb. 2010, 18(2): 273.

U. Prakash et al., "Computerised measurement of tibiofemoral alignment", Journal of Bone & Joint Surgery (Br), vol. 83-B, No. 6, Aug. 2001, pp. 819-824.

M. Roland et al., "Virtual axis finder: a new method to determine the two kinematic axes of rotation for the tibio-femoral joint", Journal of Biomechanical Engineering, Jan. 2010, vol. 132, 9 pages.

E.A. Sled et al., "Reliability of lower limb alignment measures using an established landmark-based method with a customized computer software program", NIH Public Access, Author Manuscript, Rheumatol Int., Jan. 2011, 31(1), 71-77, 14 pages.

T. Takahashi et al., "A new computer-assisted method for measuring the tibio-femoral angle in patients with osteoarthritis of the knee", Int'l Cartilage Repair Society, Osteoarthritis and Cartilage, 2004, vol. 12, No. 3, pp. 256-259.

* cited by examiner

PATIENT-SPECIFIC, MECHANICAL SELF-LOCKING, FEMORAL AND TIBIAL SURGICAL CUTTING JIGS

CROSS-REFERENCE TO RELATED APPLICATION

This application claims priority from U.S. provisional application No. 62/628,117, filed Feb. 8, 2018.

TECHNICAL FIELD

The invention relates to jigs for guiding bone resectioning in knee replacement surgery, and to the manufacture of such jigs, such that each jig is patient-specific with custom specifications determined from MRI slices of a patient's tibio-femoral joint region.

BACKGROUND ART

Femoral and tibial surgical cutting jigs are used to guide bone resectioning in knee replacement surgery. Each jig contains both the various bone-jig contact surfaces and a cutting guide defining a cut plane. In order that the cut planes are correct when the respective jigs are installed during surgery, each jig must be custom manufactured to correspond to a patient's own femur and tibia. Magnetic resonance imaging (MRI) of a patient's tibio-femoral joint region is performed prior to surgery to define the parameters needed to manufacture patient-specific jigs.

One problem in parameterizing the surface features from the MRI scans is that the coronal, axial and sagittal view orientations of actual scans do not necessarily (and usually do not) coincide with desired orthogonal axes for creating the jig, necessitating one or more rotational transformations of the respective scan slices with simultaneous rotation of all these views (coronal, axial and sagittal). Unfortunately, a "simple" Euler transformation is insufficient to obtain the proper simultaneous rotations of the image slices because it incorrectly assumes that the planes for the coronal, axial and sagittal slices being rotated are themselves orthogonal to each other. Consequently, performing a rotation θ of a coronal slice in an x-z plane alters the axial and sagittal view coordinates as well; and likewise, for a rotation φ of an axial slice in an x-y plane, and rotation ψ of a sagittal slice in a y-z plane. With an Euler transformation, as many as 15 individual iterations of the transformation may be required before the slices in the different view planes converge to fixed values, and even then, may still be wrong.

SUMMARY DISCLOSURE

Patient-specific, femoral and tibial surgical cutting jigs for bone resection are provided that are mechanical self-locking with respect to features in the tibio-femoral joint region. Each jig is a single unitary piece combining a set of bone-jig contact surfaces and bone cutting guide defining a cut plane. The set of contact surfaces are curvilinear surfaces formed onto ends of planar fins projecting from a jig substrate. The curvilinear surfaces are positioned to abut respective lateral and medial articular surface features in the tibio-femoral joint region such that the unitary piece has one and only one mechanical self-locking position.

Bone-jig contact specifications (including any cartilage on the bone as also a part of the bone surface) are computed from a series of coronal, axial and sagittal image slices obtained by magnetic resonance imaging (MRI) of a patient's tibio-femoral joint region. MRI image slices that show specified lateral and medial articular surface features in the tibio-femoral joint region are selected. Rotational transformations of the selected coronal, axial and sagittal MRI image slices onto orthogonal jig coordinates are iteratively performed, wherein each iteration of a transformation in some specified plane of rotation is accompanied by a projection of rotated coordinates onto that plane of rotation. From these transformed image slices, patient-specific parameters are characterized for specified lateral and medial articular surface features in the tibio-femoral joint region to thereby specify a set of bone-jig contact surfaces and a cut plane. Thus, the curvilinear surfaces of each jig are characterized by custom patient-specific parameters derived from measurements from selected coronal, axial and sagittal MRI slices of the tibio-femoral joint that have been subject to iterated rotational transformations onto orthogonal jig coordinates.

Accordingly, femoral and tibial surgical jigs are manufactured having curvilinear surfaces positioned according to the transformed image slices. Each jig is in the form of a single unitary piece combining a bone cutting guide and a set of curvilinear surfaces formed onto ends of projections from a jig substrate. The curvilinear surfaces abut respective lateral and medial articular surface features in the tibio-femoral joint region of the patient such that the jig has one and only one mechanical self-locking position and the bone cutting guide defines the specified cut plane.

DETAILED DESCRIPTION

Figure 1A:
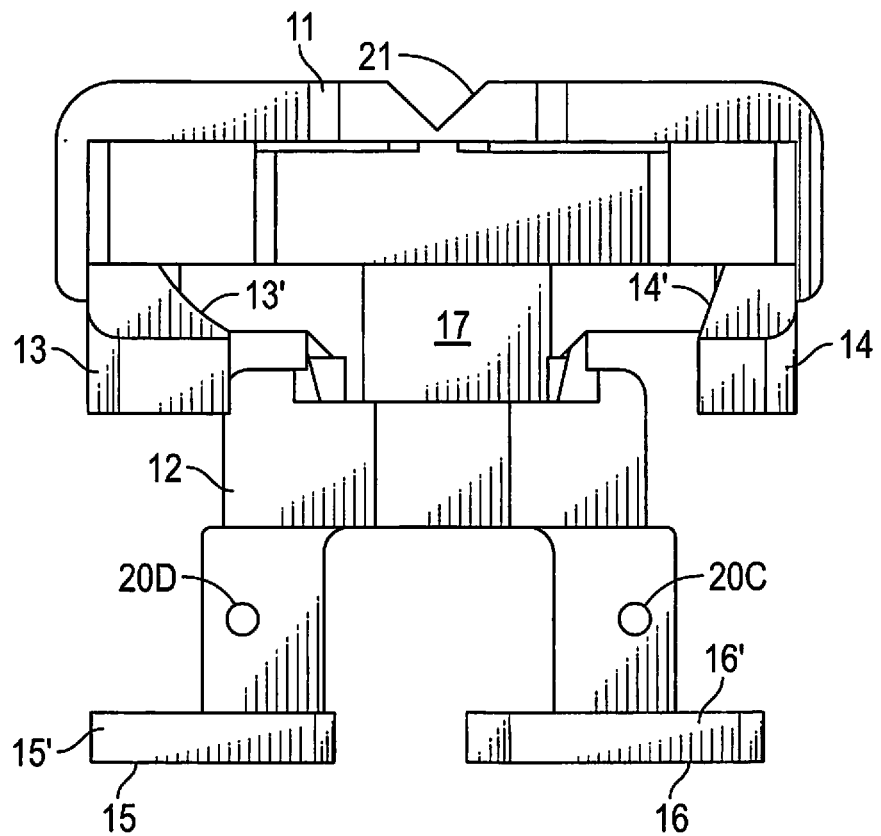
FIGS. 1A through 1F are respective front, back, right, left, top and bottom plan views of a femur jig in accord with the present invention.
Figure 1B:
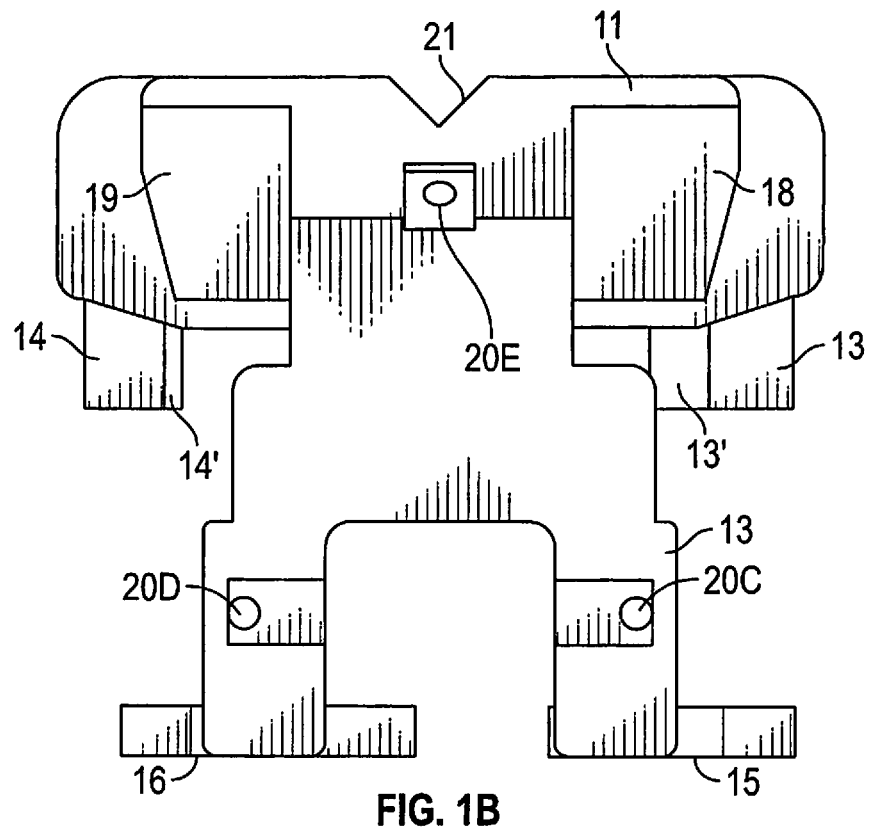
Figure 1C:
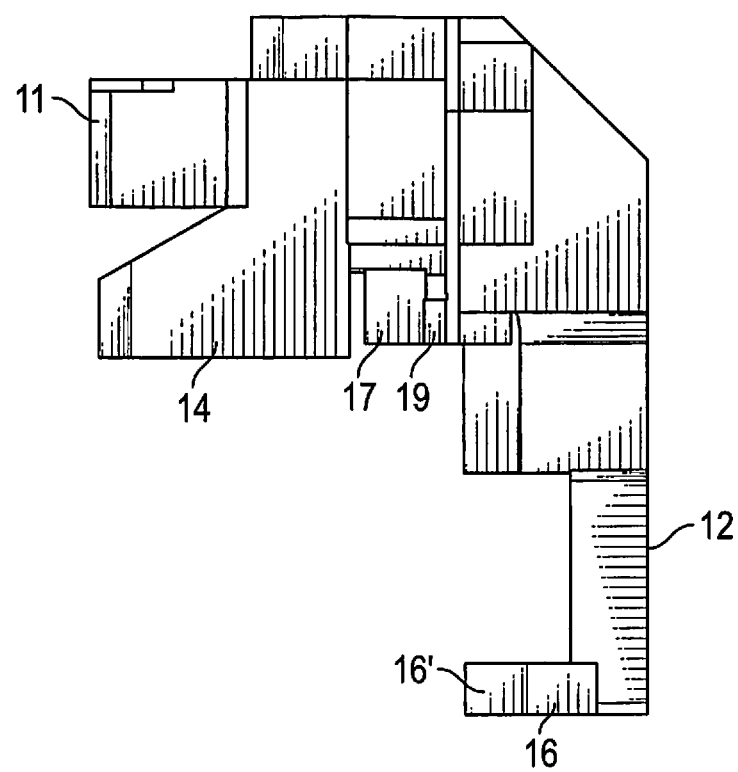
Figure 1D:
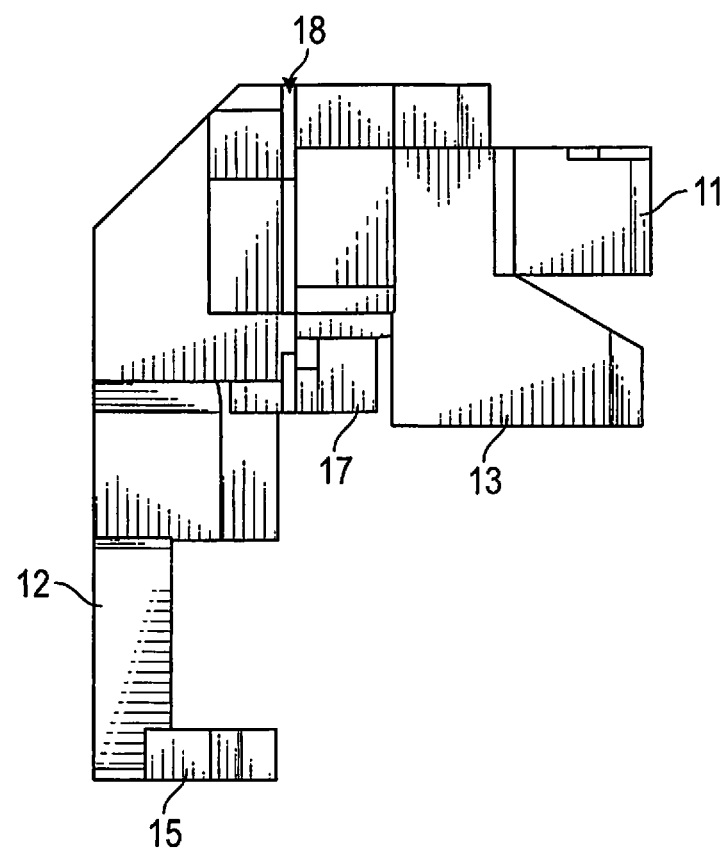
Figure 1E:
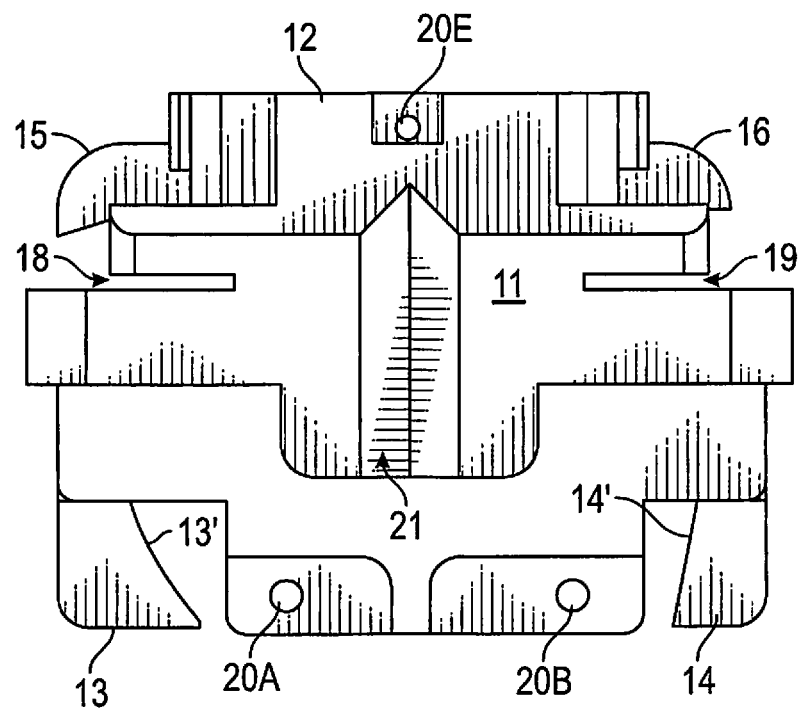
Figure 1F:
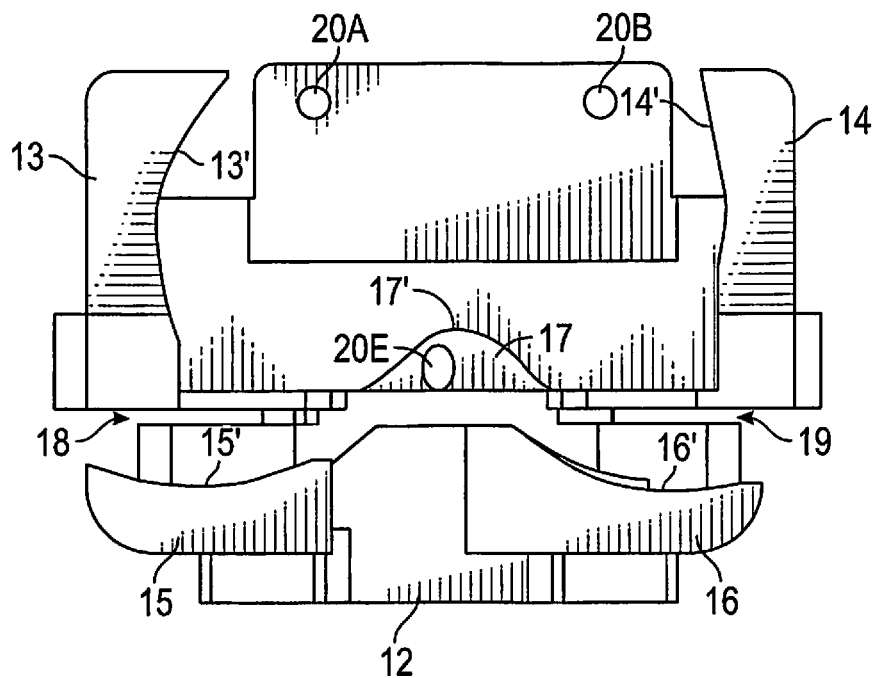
Figure 1G:
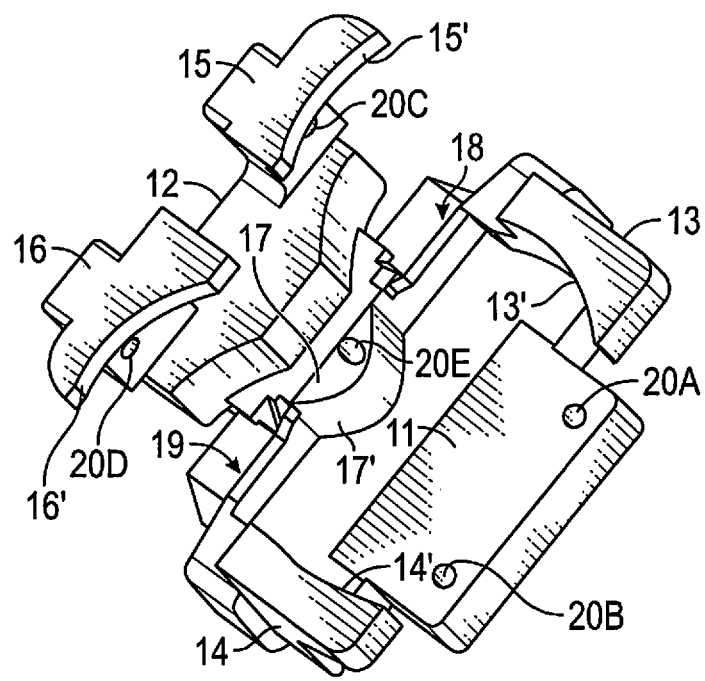
FIGS. 1G and 1H are first and second perspective views of the femur jig of FIGS. 1A through 1F.
Figure 1H:
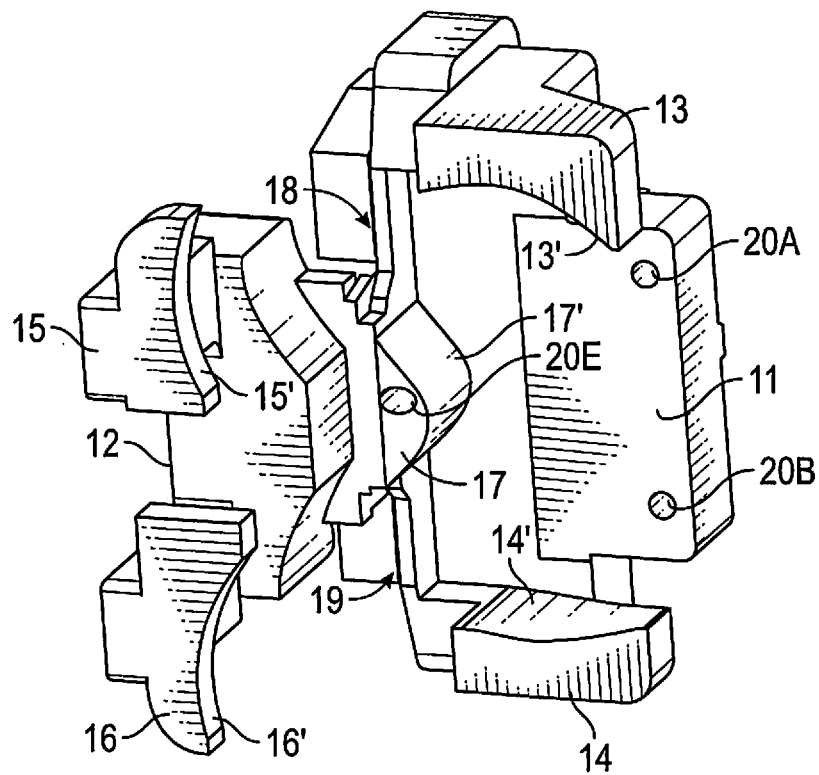
Figure 2A:
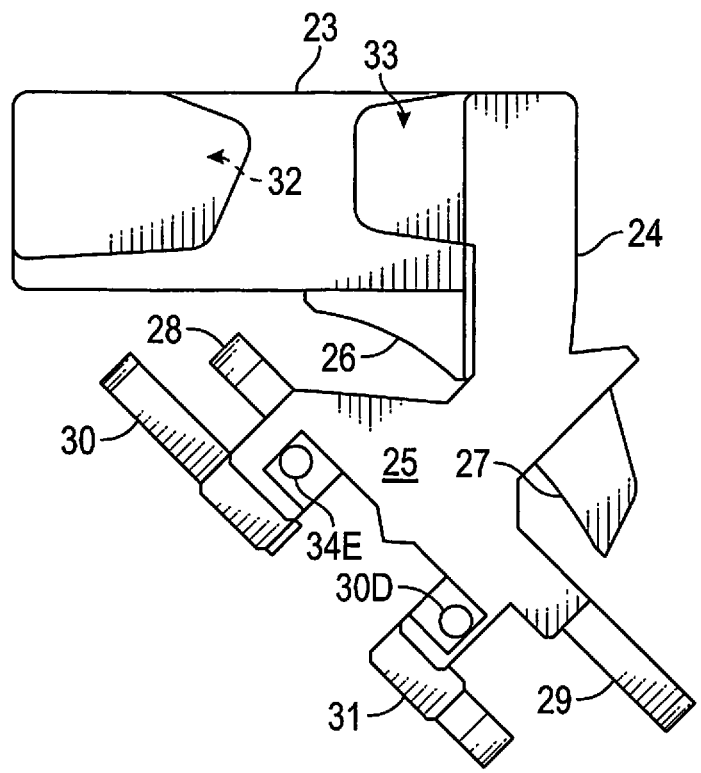
FIGS. 2A through 2F are respective front, back, right, left, top and bottom plan views of a tibia jig in accord with the present invention.
Figure 2B:
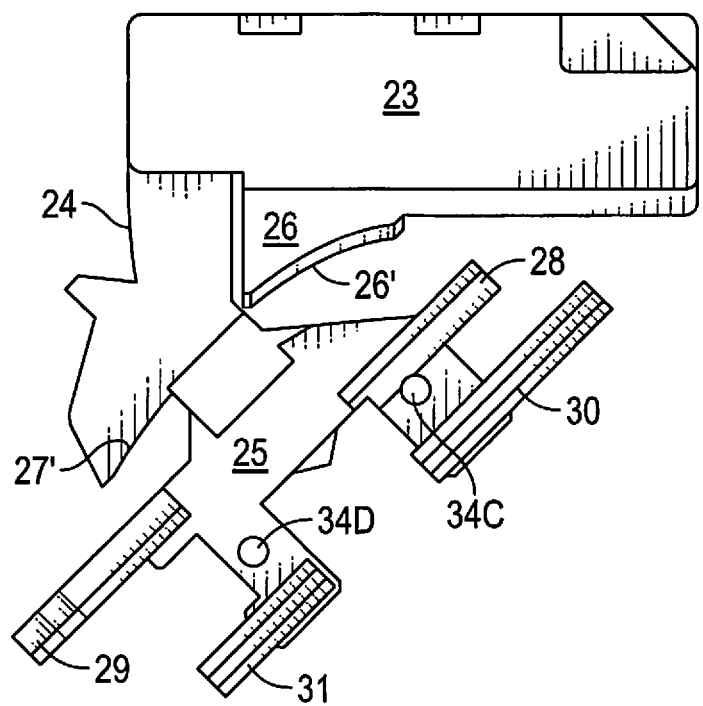
Figure 2C:
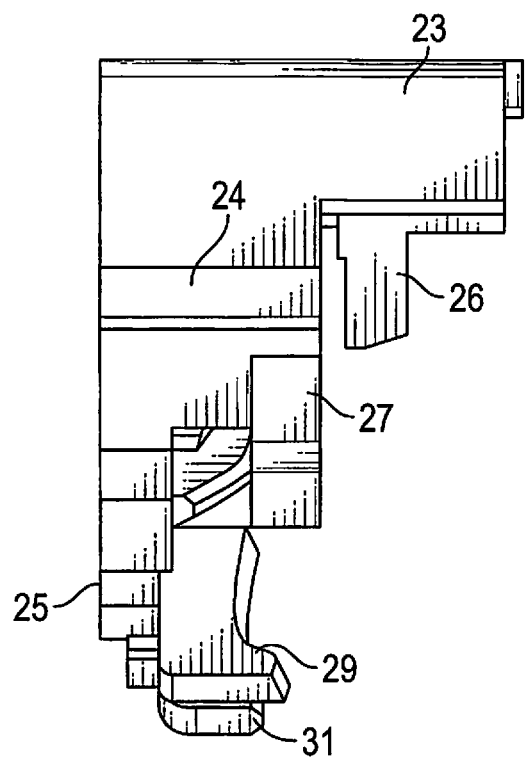
Figure 2D:
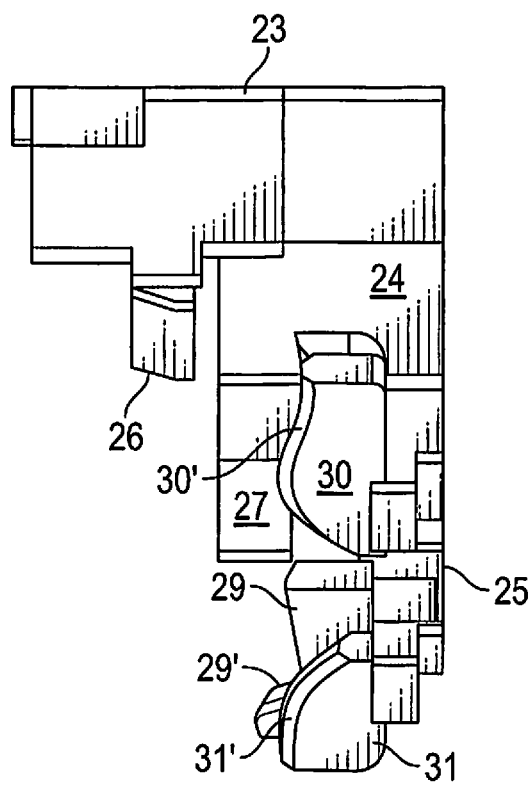
Figure 2E:
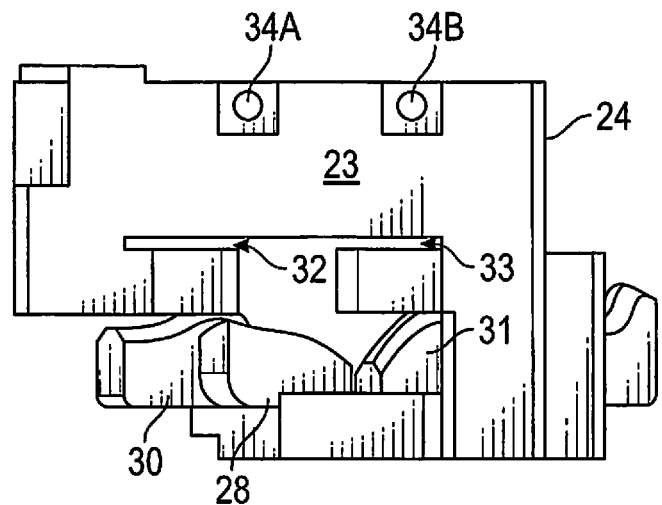
Figure 2F:
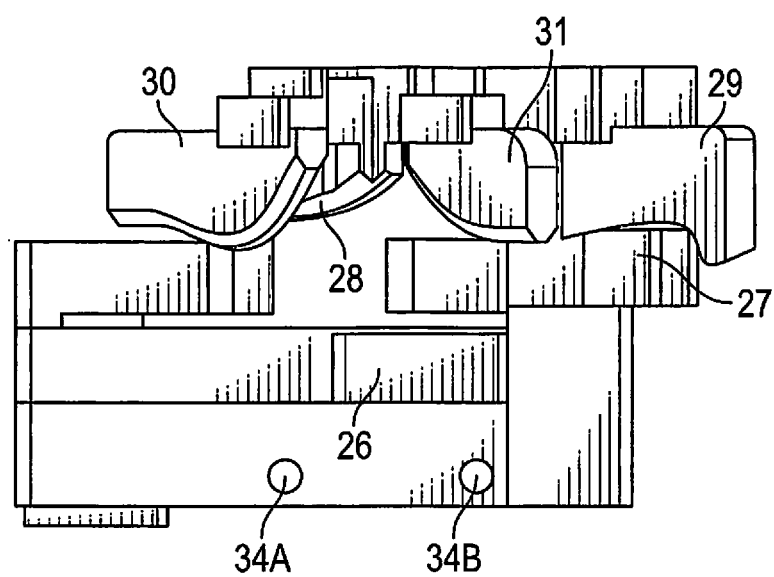
Figure 2G:
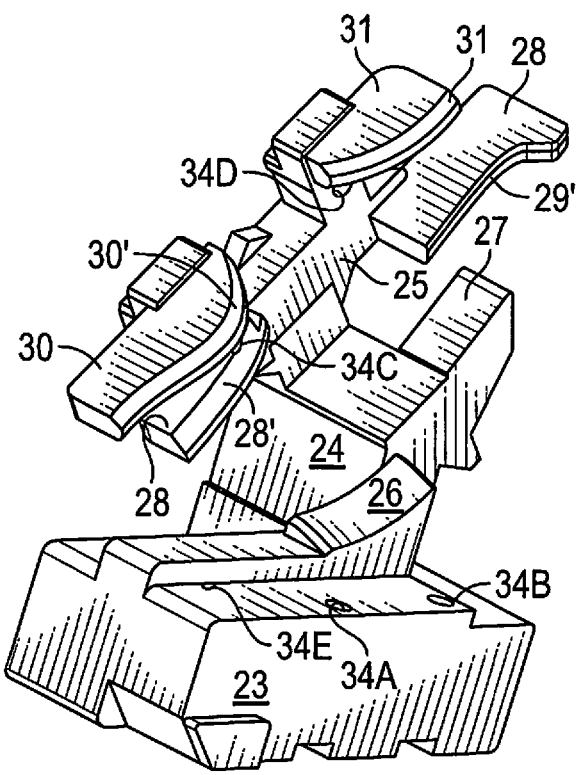
FIGS. 2G and 2H are first and second perspective views of the tibia jig of FIGS. 2A through 2F.
Figure 2H:
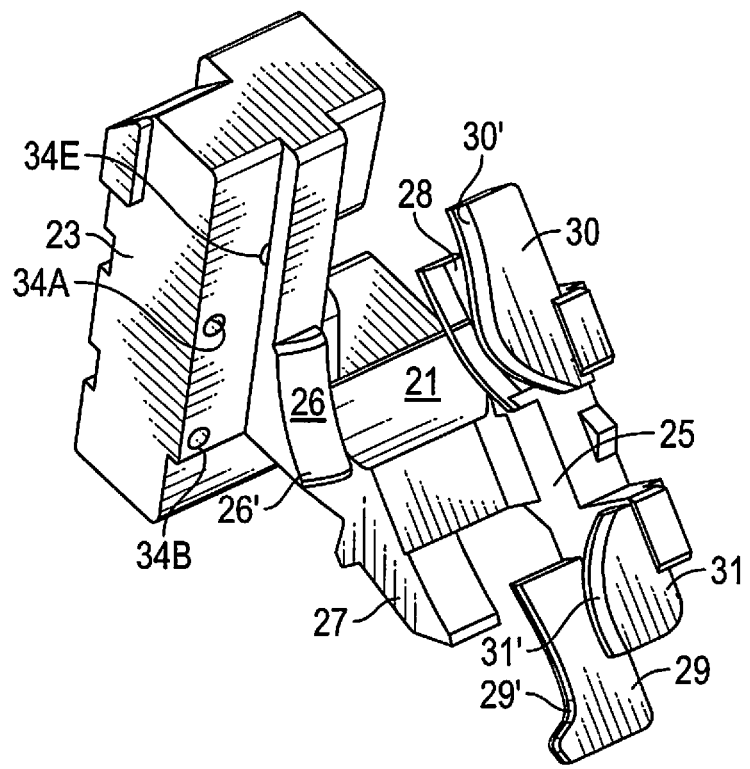

The invention relates to jigs for guiding bone resectioning in knee replacement surgery. Each jig, one for the femur and another for the tibia, contains both the various bone-jig contact surfaces and the cutting guide as a single unitary piece. For purposes of defining jig parameters, note we shall consider and treat any cartilage on the relevant bone as also constituting a part of the bone surface that the jig will contact. Hence, any reference to bone-jig contact surfaces will also include any cartilage-jig contact surfaces. The contact surfaces are curvilinear surfaces formed into ends of planar fins that project from the jig base or substrate. Each jig has three (3) pairs of contact surfaces selected to abut low-wear, lateral and medial, articular surface features, such that the jig has one and only one possible self-locking position against the bone and so the jig's integral cutting guide will define one and only one cut plane for the bone resectioning.

With reference to FIGS. 1A through 1H, a jig for guiding the resectioning of a femur is seen. The femoral jig has a front plate or block 11 that will abut against an anterior surface of the end of a femur, and an end plate or block 12 that will abut against the joint surface of the femur. The cutting guide may be in the form of two planar slots 18 and 19 extending from lateral and medial sides in the front plate or block 11. The front plate or block 11, end plate or block 12, and cutting guide 18 and 19 together form a single-piece unitary jig body of solid material that will fit against the femur in one and only one way, thereby establishing the cutting plane for the resectioning.

To ensure this single possible fitting of the jig to the femur, the respective plates or blocks 11 and 12 of the jig have sets of projections with curved contact surfaces 13' through 17' which are dimensioned according to a specific patient's bone dimensions. For the femur, medial and lateral anterior feet 13 and 14 of the femoral jig contact (a) anterior sides of the lateral and medial condyles, while medial and lateral posterior feet 15 and 16 of the jig contact (b) the distal condylar surfaces. A short posterior projection 17 from the joint of the front and end plates 11 and 12 of the jig also contacts (c) the trochlear groove surfaces. The medial and lateral anterior feet 13 and 14 extend rearward from the front plate or block 11, one on the medial side 13 and one on the lateral side 14 and have concave interior surfaces 13' and 14' whose placement and separation from one another closely match the placement and separation of the anterior sides of the respective lateral and medial condyles. Medial and lateral posterior feet 15 and 16 extend in the inferior direction from posterior ends of the end plate or block 12, again one on the medial side 15 and one on the lateral side 16 and have concave inferior surfaces 15' and 16' whose placement and separation closely match those of the respective convex, lateral and medial, distal condylar surfaces of the femur. A short posterior projection 17 extending above the end plate or block 12 at or near is junction with the front plate or block 11 has a convex curved surface 17' that contacts trochlear groove surfaces between the medial and lateral condyles of the femur. Holes 20A-20E for pins allow the jig to be secured to the femur. A notch or groove 21 in the anterior plate 11 aids in jig alignment verification.

With reference to FIGS. 2A through 2H, a jig for guiding the resectioning of a tibia is seen. The tibial jig has a main medial plate or block 23 that will abut against anterior and medial surfaces of the end of a tibia, and an end extension 25 of a front plate or block 24 that will abut against the joint surface of the tibia. The cutting guide may be in the form of two planar slots 32 and 33 extending from anterior and posterior sides of the medial plate or block 23. The medial main plate or block 23, the front plate or block 24 with its end extension 25, and the cutting guide 32 and 33 together form a single-piece unitary jig body of solid material that will fit against the tibia in one and only one way, thereby establishing the cutting plane for the resectioning. Holes 34A-34E for pins allow the jig to be secured to the tibia.

To ensure this single possible fitting of the jig to the tibia, the respective plates or blocks of the jigs have sets of projections with curved contact surfaces which are dimensioned according to a specific patient's bone dimensions. For the tibia, the main block 23 of the tibial jig contacts (a) the medial and/or anterior surface of the tibia's shaft along curved surfaces 26' and 27', while posterior feet 25 have two sets of projections 28-31 that contact (b) the superior articular surfaces of the lateral and medial condyles at positions anterior of the spine and (c) articular surfaces on lateral and medial slopes of the tibial spine itself. The presence of osteophytes generally does not adversely impact the proper fit of the jigs. Specifically, the main medial plate or block 23 has a concave extension 26 on its interior (boneward) side that contacts the medial surface of the tibia's shaft. Additionally, the front plate or block 24 may have a concave extension 27 on its lateral end that continues the curve defined by the medial block's extension and which contacts the anterior surface of the tibia's shaft. The end extension 25 projects from a superior (upper) surface of the front plate or block 24 and has a pair of posterior feet (i.e. medial and lateral feet) with respective sets of downward projections 28-31. One set of projections (one on each posterior foot), i.e. the more anteriorly located set 28 and 29, has concave curvatures 28' and 29' that contact superior articular surfaces of respective medial and lateral condyles at positions anterior of the tibial spine. The second set of projections 30 and 31 (again, one on each posterior foot) likewise has concave curvatures 30 and 31 that contact articular surfaces on respective medial and lateral slopes of the tibial spine itself.

Figure 3:
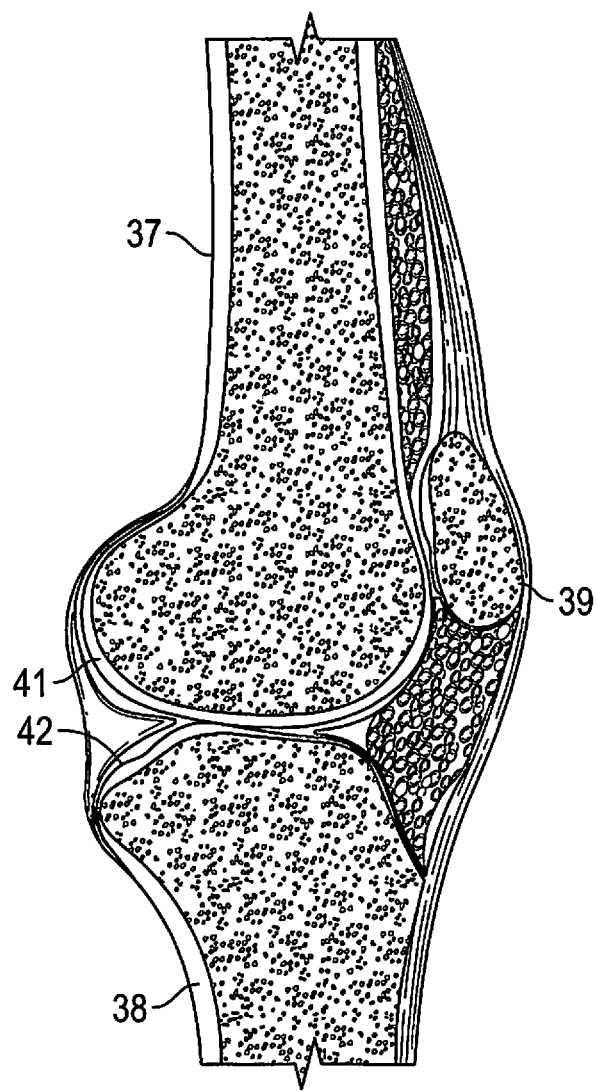
FIG. 3 is a sagittal section of a right knee joint.
Figure 4:
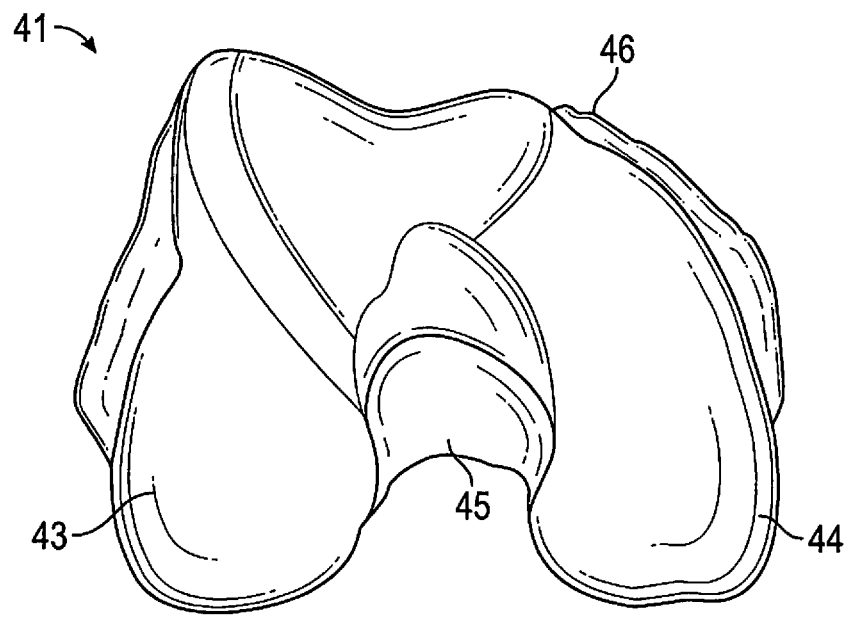
FIG. 4 is a plan view of a lower extremity of a right femur.
Figure 5:
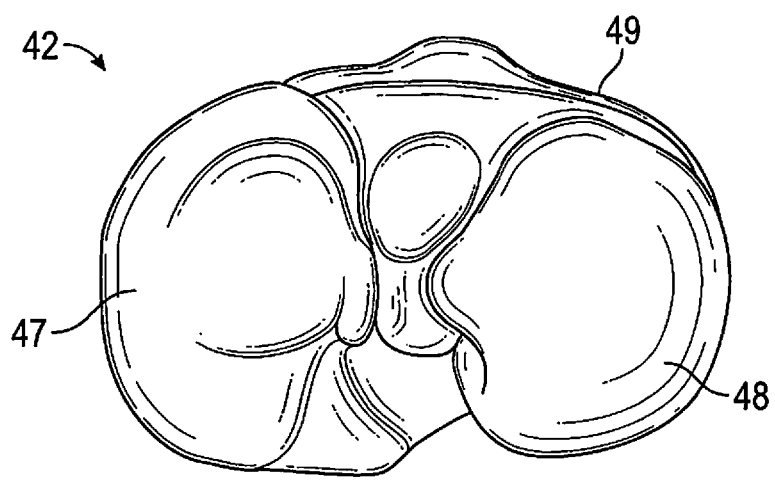
FIG. 5 is a plan view of an upper extremity of a right tibia.

FIGS. 3, 4 and 5 illustrate the features near the knee joint with which the jigs make contact. In FIG. 3, the lower portion of the femur 37 and the upper portion of the tibia are seen to meet at respective joint surfaces 41 and 42. The location of the patella 39 and corresponding connecting ligaments is also visible. In FIG. 4, the lower extremity 41 of the femur is seen to include a lateral condyle 43 and medial condyle 44 with an intercondylar region forming a trochlear groove 45. The anterior surface of the femur is at the region 46. In FIG. 5, the upper extremity 42 of the tibia is likewise seen to have both a medial condyle 47 and a lateral condyle 48. The anterior surface of the tibia is at the region 49.

Figure 6A:
FIGS. 6A through 6C are respective coronal, axial and sagittal MRI scan images of a knee joint.
Figure 6B:
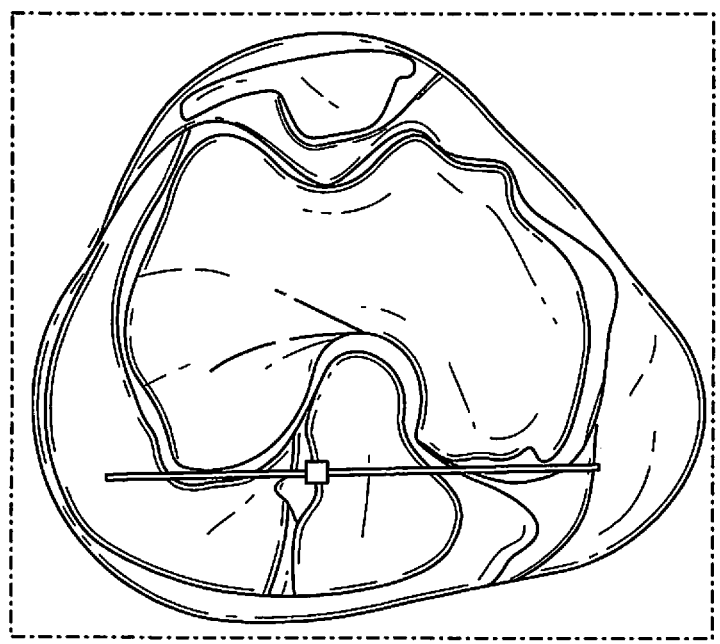
Figure 6C:
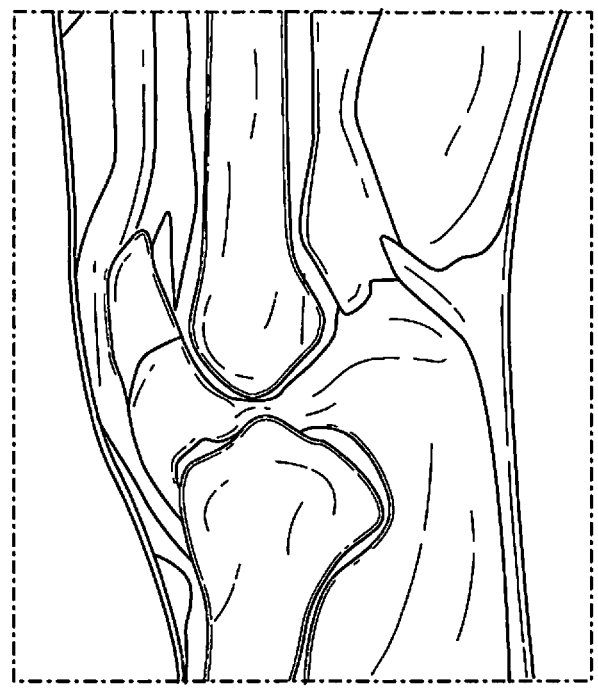

One aspect of the invention is that each jig is patient-specific with custom dimensions determined from MRI slices of the patient's tibio-femoral joint region. Three series of MRI slices are taken of the knee to create respective coronal (front), axial (top) and sagittal (side) views, respectively seen in FIGS. 6A, 6B and 6C. Each "slice" is actually 2 to 3 mm thick and there is about a 1 mm gap between successive slices of the same view angle. Besides slices of the knee, it may be advantageous to obtain at least coronal MRI scans of the femur/hip and tibia/ankle areas as well to fully characterize the lower limb alignment. But in comparison to computationally-intensive full segmentation approaches, only a select small number of slices of the knee joint area (5 or 6 for each bone) are needed to identify and parameterize the articular surface features for constructing the jigs. These are slices associated with low wear portions of the lateral and medial condyle surfaces and the intercondylar regions (with the trochlear groove and tibial spine), seen especially well in the coronal view (FIG. 6A). Axial and sagittal views (FIGS. 6B and 6C) can define anterior surfaces of the bones immediately adjacent to the joint.

Figure 7:
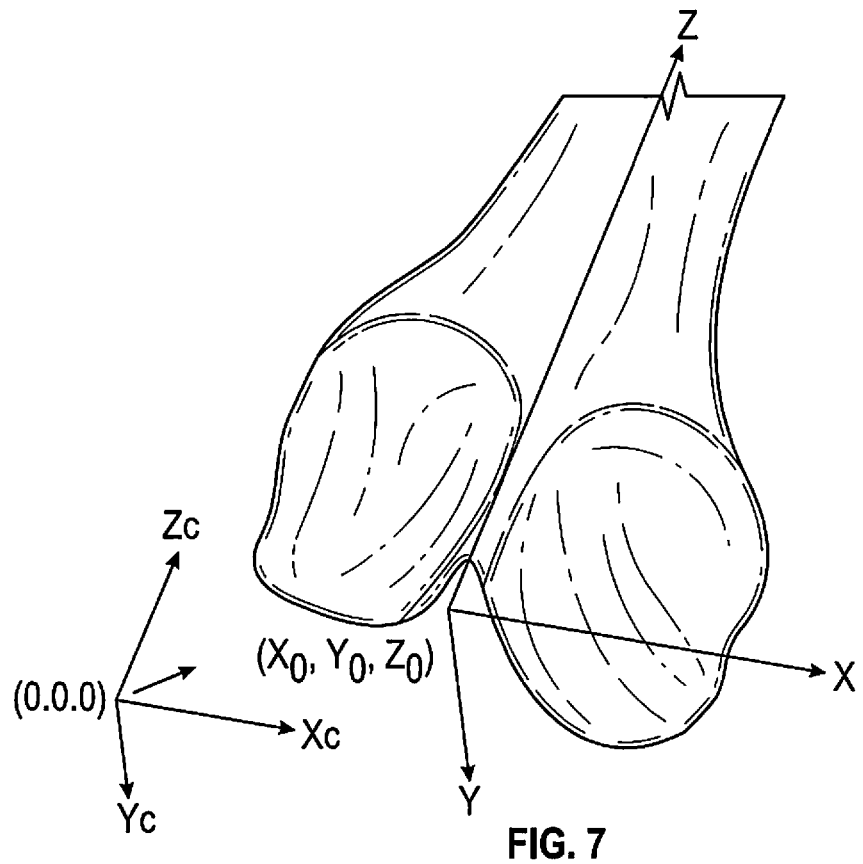
FIG. 7 is a perspective a femur illustrating scan and translated coordinate axes.
Figure 8C:
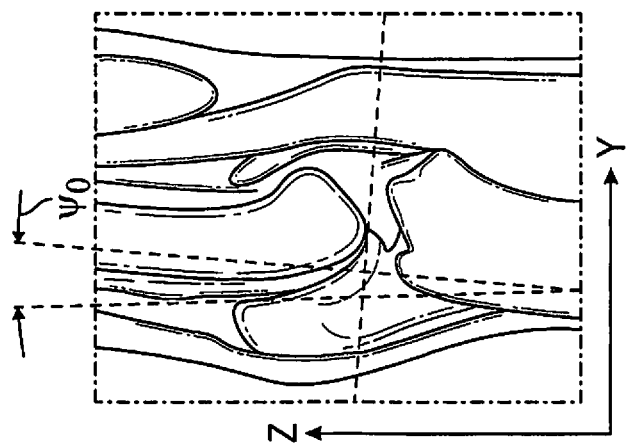
FIGS. 8A through 8C are respective coronal, axial and sagittal translated scan images showing coordinate planes and rotation angles overlaid upon the images.
Figure 8B:
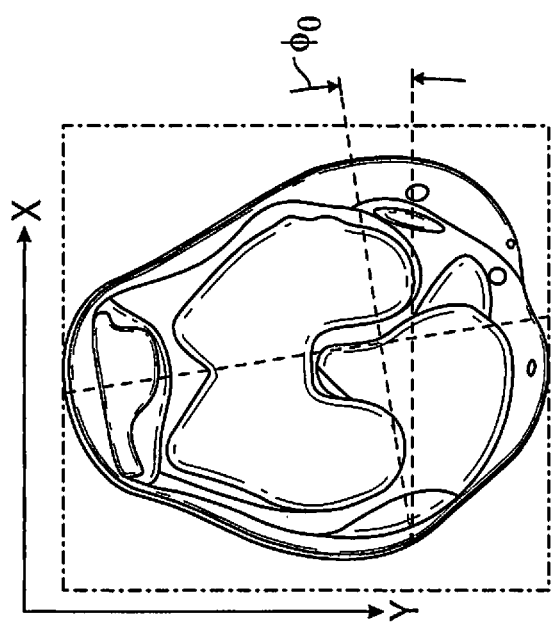
Figure 8A:
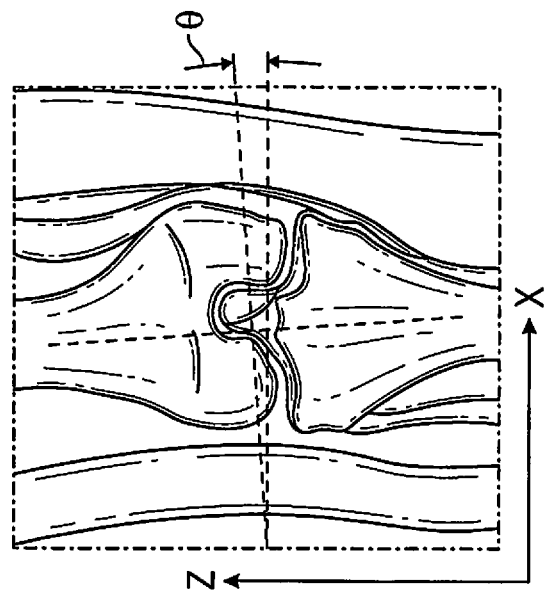

With reference to FIG. 7, one problem in parameterizing the surface features from the MRI scans is that the coronal, axial and sagittal view orientations of actual scans do not necessarily (and usually do not) coincide with desired orthogonal axes (x, y, z) for creating the jig, necessitating one or more rotational transformations (θ, φ, ψ) of the respective scan slices. Unfortunately, a "simple" Euler transformation is insufficient to obtain the proper rotations of the image slices because it incorrectly and simultaneously assumes that the planes for the actual coronal (x-z), axial (x-y) and sagittal (y-z) image slices being rotated are themselves orthogonal to each other. Consequently, performing a rotation θ of a coronal slice in an x-z plane alters the axial and sagittal view coordinates as well; and likewise, for a rotation φ of an axial slice in an x-y plane, and rotation ψ of a sagittal slice in a y-z plane. With an Euler transformation, as many as 15 iterations of the transformation may be required before the slices in the different view planes converge to fixed values, and even then, may still be wrong.

Figure 9A:
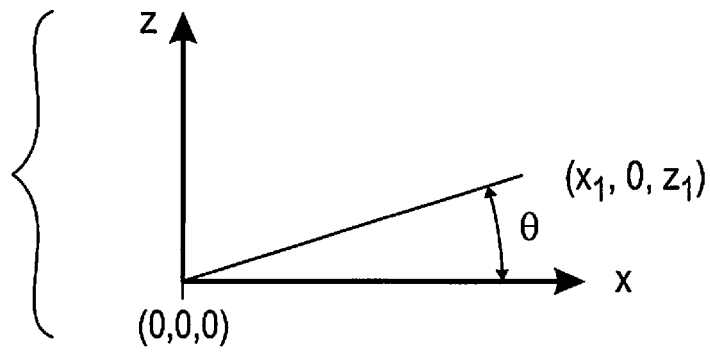
FIGS. 9A through 9C are views of original and transformed coordinate axes for respective coronal, axial and sagittal rotational transformations.
Figure 9B:
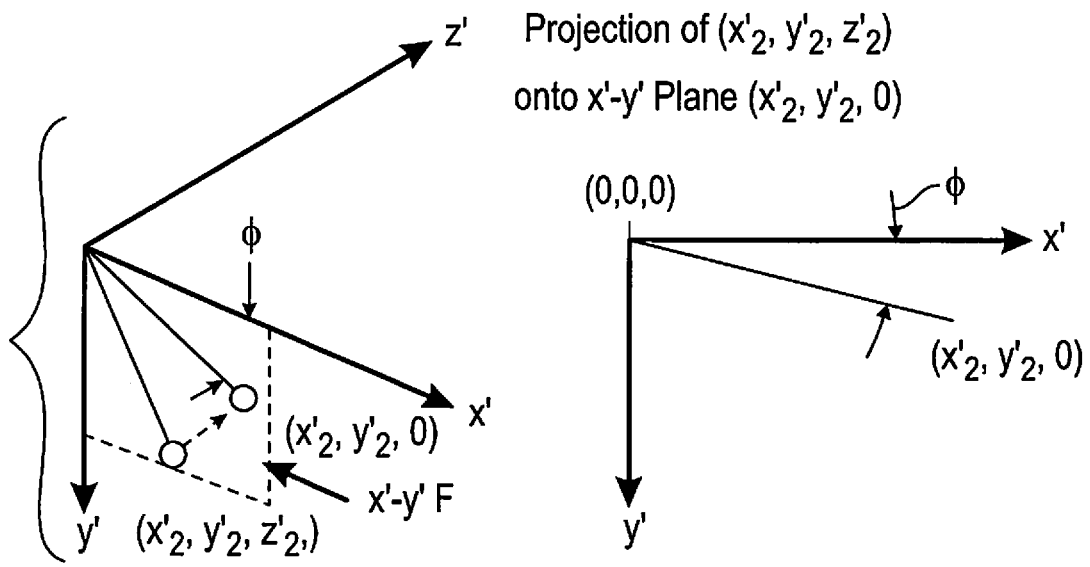
Figure 9C:
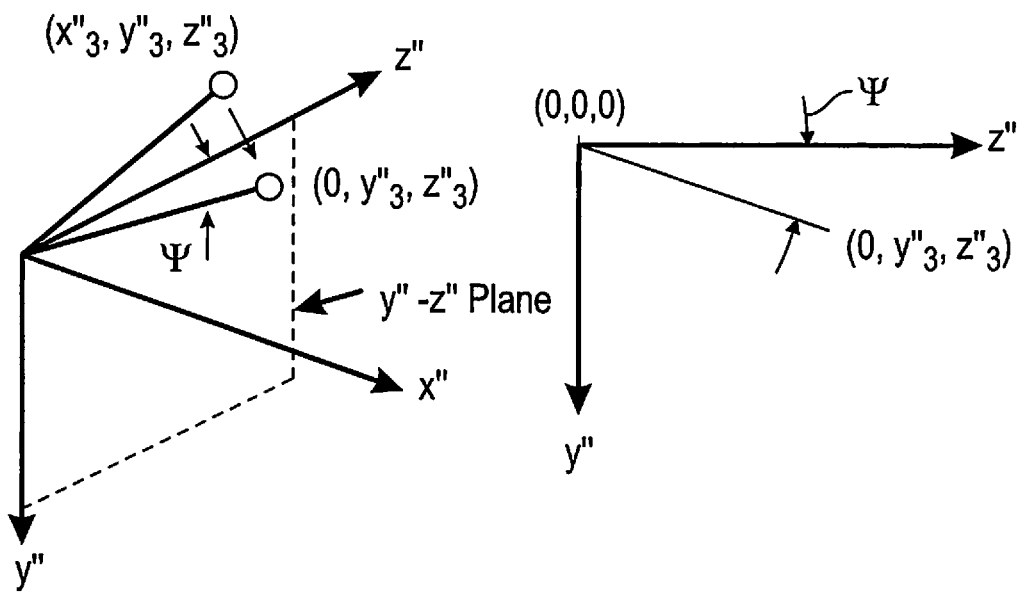

With reference to FIGS. 9A, 9B and 9C, an improved rotational transformation method for converting the scan views into the desired proper axes reduces the number of iterations to three and produces parameters that correspond much more closely to the joint surfaces in the desired jig coordinates. The improved transformation matrix is based not only on planar rotations (as in Euler), but also on a projection of the rotated coordinates onto the plane of rotation (e.g., projection of x', y', z' coordinates—obtained from x-y plane rotation θ to an x'-y' plane—onto x', y', 0 coordinates) before proceeding to the next rotation.

We begin with a translation of the scan origin $(x_0, y_0, z_0)$ to a specified center $(x_c, y_c, z_c)$ of the joint anatomy, such as the intercondylar space where the anterior cruciate ligament attaches to the tibia.

$$\begin{bmatrix} x \\ y \\ z \end{bmatrix} = \begin{bmatrix} A_{11} & A_{12} & A_{13} \\ A_{21} & A_{22} & A_{23} \\ A_{31} & A_{32} & A_{33} \end{bmatrix} \begin{bmatrix} x_c \\ y_c \\ z_c \end{bmatrix} + \begin{bmatrix} \Delta x \\ \Delta y \\ \Delta z \end{bmatrix} \text{ where } \begin{bmatrix} \Delta x \\ \Delta y \\ \Delta z \end{bmatrix} = \begin{bmatrix} -x_0 \\ -y_0 \\ -z_0 \end{bmatrix}.$$

Next, we rotate the coordinates with respect to the newly centered origin. The rotations can be performed in any order, but we start with a coronal rotation θ about the x-z plane, followed by an axial rotation φ about a transformed x'-y' plane, then sagittal rotation ψ about a further transformed y"-z" plane.

The first rotation is represented in FIG. 9A. The coronal rotation θ about the x-z plane transforms the x-axis to an x'-axis extending from (0, 0, 0) to $(x_1, 0, z_1)$, where $\theta = \tan^{-1}(z_1/x_1)$.

$$\Theta = \begin{bmatrix} \cos\theta & 0 & -\sin\theta \\ 0 & 1 & 1 \\ \sin\theta & 0 & \cos\theta \end{bmatrix}$$

An x-y plane point transformation to x', y', z' coordinates follows:

$$\begin{bmatrix} x'_2 \\ y'_2 \\ z'_2 \end{bmatrix} = \begin{bmatrix} \cos\theta & 0 & -\sin\theta \\ 0 & 1 & 1 \\ \sin\theta & 0 & \cos\theta \end{bmatrix} \begin{bmatrix} x_2 \\ y_2 \\ 0 \end{bmatrix} = \begin{bmatrix} \cos\theta \cdot x_2 \\ y_2 \\ \sin\theta \cdot x_2 \end{bmatrix}$$

A y-z plane point transformation to x', y', z' coordinates follows:

$$\begin{bmatrix} x'_3 \\ y'_3 \\ z'_3 \end{bmatrix} = \begin{bmatrix} \cos\theta & 0 & -\sin\theta \\ 0 & 1 & 1 \\ \sin\theta & 0 & \cos\theta \end{bmatrix} \begin{bmatrix} 0 \\ y_3 \\ z_3 \end{bmatrix} = \begin{bmatrix} -\sin\theta \cdot z_3 \\ y_2 \\ \cos\theta \cdot z_3 \end{bmatrix}$$

The second rotation is represented by FIG. 9B. The axial rotation φ transforms the x'-axis to an x"-axis extending from (0,0,0) to $(x'_2, y'_2, 0)$, where $\varphi = \tan^{-1}(y'_2/x'_2) = \tan^{-1}(y_2/\cos\theta \cdot x_2)$.

$$\Phi = \begin{bmatrix} \cos\varphi & -\sin\varphi & 0 \\ \sin\varphi & \cos\varphi & 0 \\ 0 & 0 & 1 \end{bmatrix}$$

An y'-z' plane point transformation to x", y", z" coordinates follows:

$$\begin{bmatrix} x''_3 \\ y''_3 \\ z''_3 \end{bmatrix} = \begin{bmatrix} \cos\varphi & -\sin\varphi & 0 \\ \sin\varphi & \cos\varphi & 0 \\ 0 & 0 & 1 \end{bmatrix} \begin{bmatrix} x'_3 \\ y'_3 \\ z'_3 \end{bmatrix} = \begin{bmatrix} -\sin\theta \cdot \cos\varphi \cdot z_3 - \sin\varphi \cdot y_3 \\ -\sin\varphi \cdot \sin\theta \cdot z_3 + \cos\varphi \cdot y_3 \\ \cos\theta \cdot z_3 \end{bmatrix}.$$

The third rotation is represented by FIG. 9C. The sagittal rotation ψ transforms the z"-axis to an z'"-axis extending from (0, 0, 0) to $(0, y'''_3, z'''_3)$, where $\psi = \tan^{-1}(y'''_3/z'''_3) = \tan^{-1}[(-\sin\varphi \cdot \sin\theta \cdot z_3 + \cos\varphi \cdot y_3)/\cos\theta \cdot z_3]$.

$$\Psi = \begin{bmatrix} 1 & 0 & 0 \\ 0 & \cos\psi & -\sin\psi \\ 0 & \sin\psi & \cos\psi \end{bmatrix}$$

Yet another plane point transformation to x'", y'", z'" coordinates follows:

$$\begin{bmatrix} x''' \\ y''' \\ z''' \end{bmatrix} = \begin{bmatrix} 1 & 0 & 0 \\ 0 & \cos\psi & -\sin\psi \\ 0 & \sin\psi & \cos\psi \end{bmatrix} \begin{bmatrix} x'' \\ y'' \\ z'' \end{bmatrix} = \begin{bmatrix} A_{11} & A_{12} & A_{13} \\ A_{21} & A_{22} & A_{23} \\ A_{31} & A_{32} & A_{33} \end{bmatrix} \begin{bmatrix} x \\ y \\ z \end{bmatrix}$$

where:

$A_{11} = \cos\varphi \cdot \cos\theta$ $A_{12} = -\sin\varphi$ $A_{13} = -\cos\varphi \cdot \sin\theta$ $A_{21} = \cos\psi \cdot \sin\varphi \cdot \cos\theta - \sin\psi \cdot \sin\theta$ $A_{22} = -\cos\psi \cdot \sin\varphi - \sin\psi \cdot \cos\varphi$ $A_{23} = -\cos\psi \cdot \sin\varphi \cdot \sin\theta - \sin\psi \cdot \cos\theta$ $A_{31} = \sin\psi \cdot \sin\varphi \cdot \cos\theta + \cos\psi \cdot \sin\theta$ $A_{32} = \sin\psi \cdot \cos\varphi$ $A_{33} = -\sin\psi \cdot \sin\varphi \cdot \sin\theta + \cos\psi \cdot \cos\theta$ This process successive rotations and projections is then iterated a number of times until changes in transformed images reduce below specified thresholds ε.

$$\begin{bmatrix} x''' \\ y''' \\ z''' \end{bmatrix}_{i+1} = \begin{bmatrix} A_{11} & A_{12} & A_{13} \\ A_{21} & A_{22} & A_{23} \\ A_{31} & A_{32} & A_{33} \end{bmatrix}_i \begin{bmatrix} x \\ y \\ z \end{bmatrix}_i$$

where i=1, 2, 3, . . . .

$$T_i = \begin{bmatrix} A_{11} & A_{12} & A_{13} \\ A_{21} & A_{22} & A_{23} \\ A_{31} & A_{32} & A_{33} \end{bmatrix}_i$$

$$F = \prod_i^n T_{n-i+1},$$

where F is total transformation matrix, n is total number of transformations and $T_{n-i+1}$ is $(n-i+1^{st})$ transformation matrix. Combining the separate transformations into a total transformation matrix is possible here even where the original coronal, axial and sagittal image views are not actually orthogonal to one another. The iteration criteria (which can be different for the coronal, axial and sagittal views; for example, more stringent for the coronal view and least stringent for the sagittal view) are:

$|\theta_{i+1} - \theta_i| < \varepsilon_c$ $|\varphi_{i+1} - \varphi_i| < \varepsilon_a$ $|\psi_{i+1} - \psi_i| < \varepsilon_s$ Once the image has been properly transformed, the various dimensions of joint features for the femur and tibia can readily be calculated and used to construct the femoral and tibial jigs of FIGS. 1 and 2.

Figure 10A:
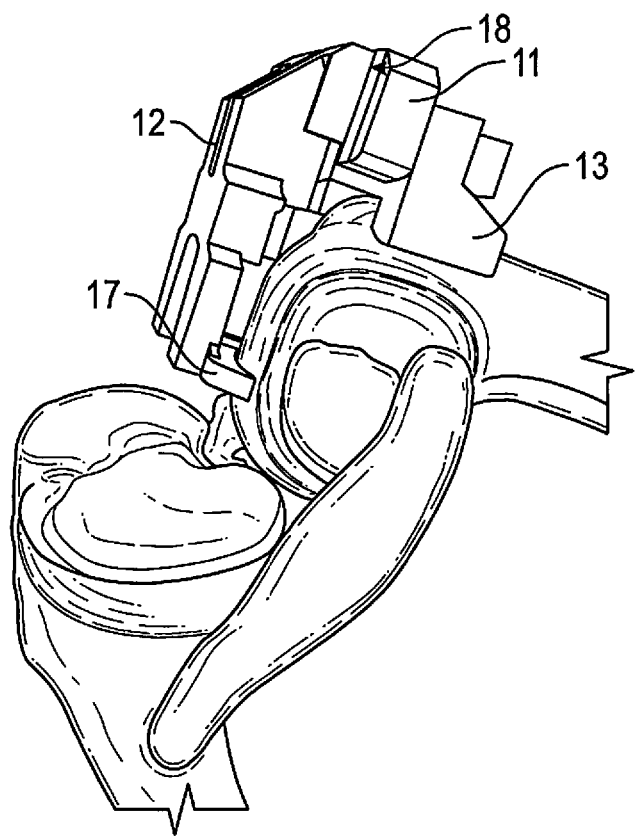
FIGS. 10A through 10D are perspective views of femoral jig and femur that illustrate steps in aligning the femur jig and securing the jig to the femur with pins.
Figure 10B:
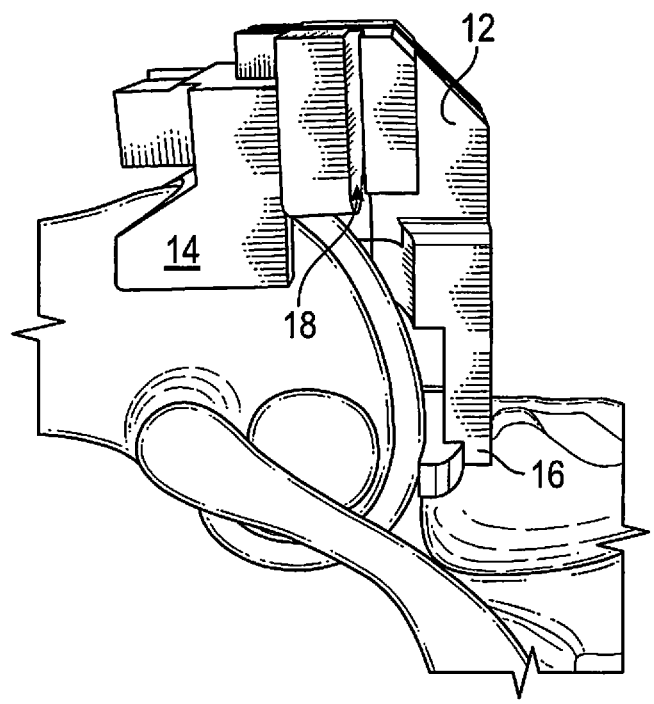
Figure 10C:
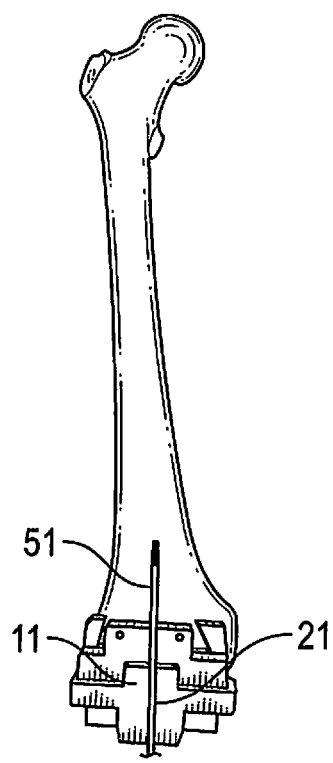
Figure 10D:
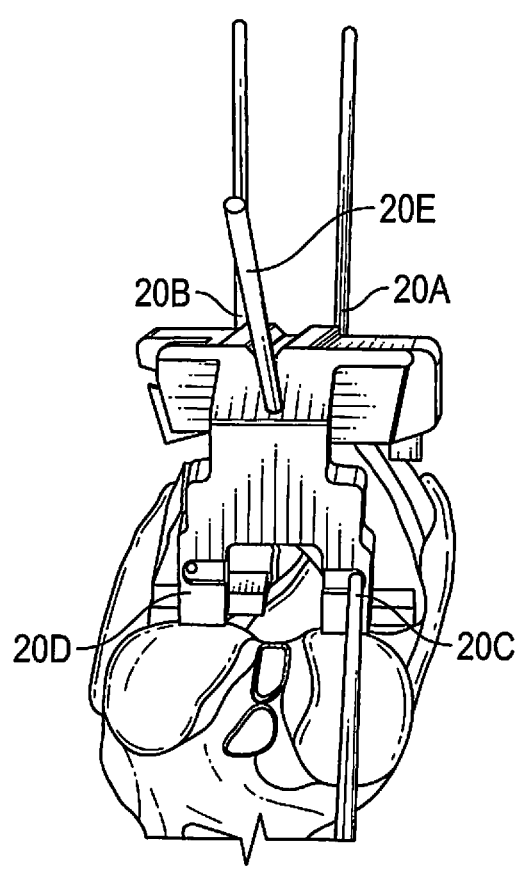

With reference to FIGS. 10A through 10D, the femoral jig or guide is installed onto the femur during surgery according to a carefully prescribed procedure. The jig, if constructed according to the transformed MRI scan images will fit one and only one way onto the end of the femur as defined by the curved contact surfaces of the jig. With the knee moderately flexed, the medial synovium is released from the mid-point of the patella proximally to a point superior to the trochlear groove. The posterior patellar tendon fat pad is excised from the joint line to the tibial tubercle. With the knee flexed to approximately 70°, retract the quadriceps muscle in the usual fashion to expose the anterior femoral cortex. Displace the patella laterally as usual to obtain full exposure. Removal of osteophytes is at the surgeon's option and their presence is generally not a detriment to proper fit of the guides (due to the choice of contact points of the jig contact surfaces to low-wear regions on the femur). Likewise, removal of osteophytes does not adversely impact guide fit. Place the femoral jig or guide onto the end of the femur. Initial placement is accomplished by orienting the guide and the condyle contact feet 15 and 16 slightly above the mid-point of the condylar curve as to allow the superior feet to make initial contact with the epicondylar area. While maintaining light pressure on the guide, rotate it posteriorly until anterior feet 13 and 14 and posterior feet 15 and 16 of the guide make light contact with the anterior lateral and medial sides of the condyles and the distal condylar surfaces, as shown in FIG. 10A. From the medial and lateral sides, the curved contacts 13, 14, 15 and 16 should light touch the surface of the tissue without using excess force or direct pressure. A small (less than 1 mm) gap may sometimes occur somewhere along the contact curves. An additional contact 17 in the trochlear groove will not be visible. A visual indicator in the form of a V-shaped notch or slot 21 verifies that the guide is correctly aligned with respect to the long axis of the femur. When properly placed, a pin 51 placed in this notch 21 will point toward the center of the femoral head, as seen in FIG. 10C. Additionally, it will be seen to be located directly over the midpoint of the condylar notch. Once all of the positioning points are correctly verified the projected cut plane defined by the planar cutting guide slots 18 and 19 in the jig should be assessed before proceeding, for example by employing a resection checker or "angel-wing" passed through the cut slot. The depth of both the medial and lateral cuts should verified as they affect the varus/valgus angle. Additionally, resectioning along the defined cut plane should not lead to notching or gapping of the implant following use of a 4:1 (chamfer) cutting block. As seen in FIG. 10B, the final anterior cut plane should just skim the anterior surface of the femur. After verification of the cuts, distal pins are placed through holes 20A and 20B while holding the jig in place. Using care that the guide is not skewed or flexed, anterior pins are placed through holes 20C and 20D while still holding the jig in place. After removal of the lateral distal pin, it is relocated to a diagonal stabilization pin location through hole 20E to reduce the possible guide shifting due to saw vibration. The medial distal pin is left in place until the lateral condyle cut is complete. After the lateral femur condyle pin is removed, the lateral condyle itself is removed using an orthopedic saw, as seen in FIG. 10D. A saw blade of at least 110 mm length will likely be needed to fully reach through the condyle in some cases. A blade thickness of 1.27 mm is recommended.

Figure 11A:
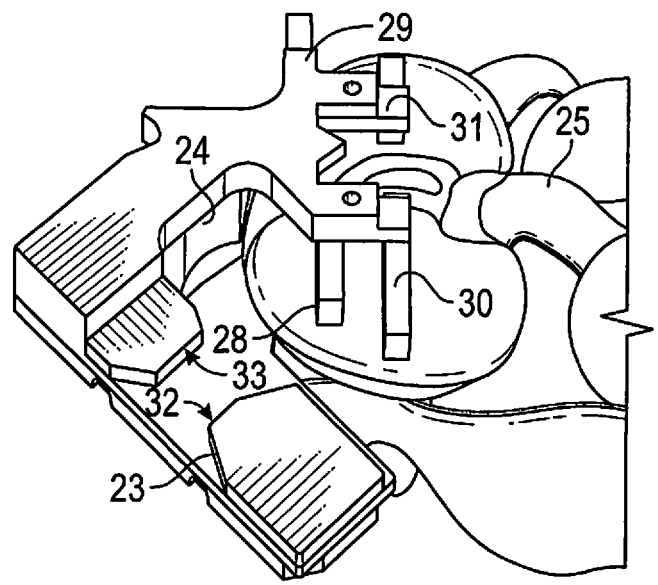
FIGS. 11A through 11C are perspective views of tibial jig and tibia that illustrate steps in aligning the tibial jig and securing the jig to the tibia with pins.
Figure 11B:
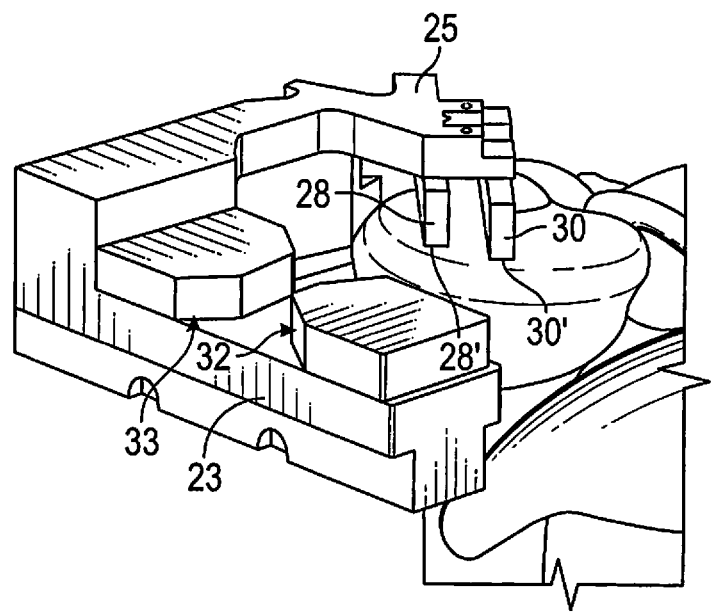
Figure 11C:
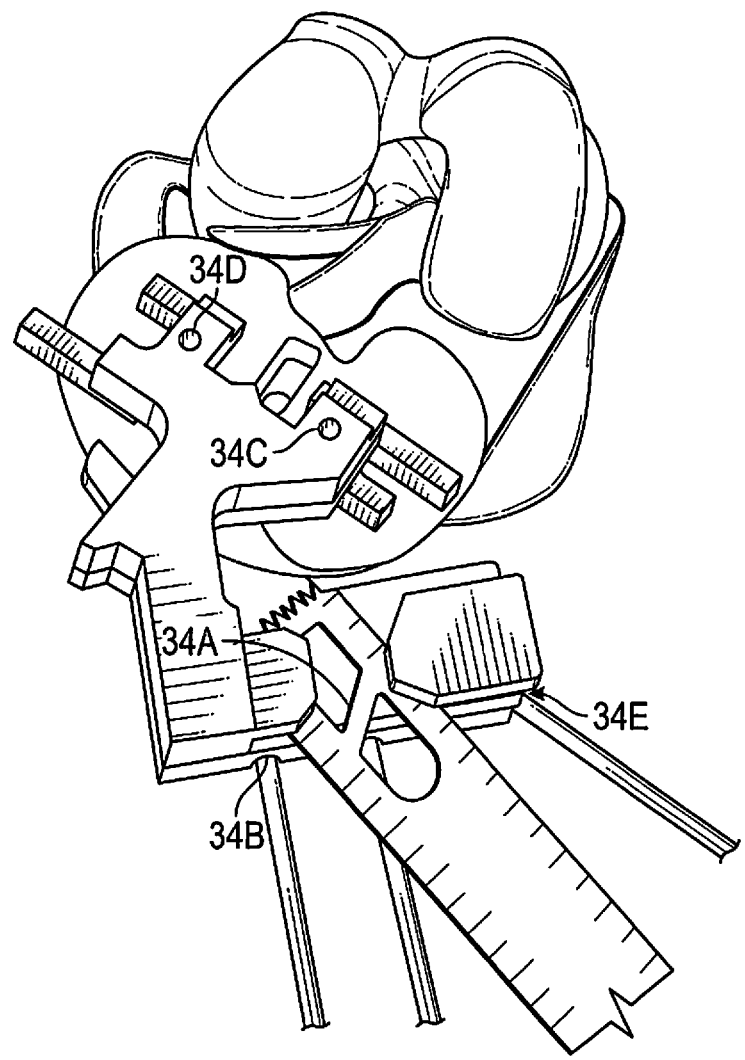

With reference to FIGS. 11A-11C, next, the tibial jig or guide is installed onto the tibia during surgery according to a carefully prescribed procedure. The jig, if constructed according to the transformed MRI scan images will fit one and only one way onto the end of the tibia as defined by the curved contact surfaces of the jig. The jig is placed against the medial and anterior side surfaces of the tibia and the top of the tibial plateau with the medial plate or block 23 against the medial side surface of the tibia, the anterior plate or block 24 against the anterior side surface of the tibia, and the posterior foot extension 25 with wing projections 28-31 above the tibial plateau. For the medial and anterior sides of the tibia, the curved contacts 26 and 27 abut the tibia as seen from above in FIG. 11A. For the tibial plateau, the curved underside of the medial projections 28 and 30 contact the medial condyles of the tibia at respective anterior and posterior positions, as seen if FIG. 11B. Likewise, the curved underside of the lateral projections 29 and 31 will contact the lateral condyles of the tibia at respective anterior and posterior positions. While holding the jig in place, proximal pins are inserted through holes 34C and 34D, then anterior pins are inserted through holes 34A and 34B. The proximal pins may then be removed, and the jig stabilized by installing one of them through the diagonal hole 34E at the posterior end of the medial plate 23. After re-verifying the cut angle (medial/lateral and posterior slopes) is correct, the tibia may be cut as seen in FIG. 11C by inserting the saw into cut plane slots 32 and 33. Once the end of the tibia has been completely cut, the pins and tibial jig are removed, and the remainder of the total knee replacement surgery can continue.

What is claimed is:

1. A surgical jig for bone resection in a tibio-femoral joint region, comprising:

a single unitary piece combining a set of bone jig contact surfaces and a bone cutting guide defining a cut plane, the set of contact surfaces being curvilinear surfaces formed onto ends of projections from a jig substrate, the curvilinear surfaces positioned to abut respective lateral and medial articular surface features in the tibio-femoral joint region such that the unitary piece has one and only one mechanical self-locking position, the curvilinear surfaces further characterized by custom patient-specific parameters derived from measurements from selected coronal, axial and sagittal magnetic resonance imaging (MRI) image slices of the tibio-femoral joint, the image slices having been subject to a set of rotational transformations onto orthogonal jig coordinates including at least one coronal rotation, at least one axial rotation, and at least one sagittal rotation, wherein each transformation in some specified plane of rotation is accompanied by a projection of rotated coordinates onto that plane of rotation, each coronal rotation in an x-z plane by an angle θ is followed by x-y and y-z plane point transformations, each axial rotation in a x-y plane by an angle φ is followed by y-z and x-z plane point transformations, and each sagittal rotation in a y-z plane by an angle Ψ is followed by x-z and x-y plane point transformation, where an x coordinate axis coincides with a lateral-medial direction, a y coordinate axis coincides with an anterior-posterior direction, and a z coordinate axis coincides with a bone long axis, each rotational transformation after a first transformation being a rotation followed by point transformations in a set of transformed planes resulting from the previous rotational transformation.

2. The surgical jig as in claim 1, wherein the jig is a femoral jig having a front plate coupled to an end plate at an elbow joint, the front plate having at least one planar slot therein coinciding with a desired cut plane when the jig is installed onto a femur, the front plate having a pair of anterior feet with curvilinear surfaces thereon for contact with anterior sides of respective medial and lateral condyles of the femur, the end plate having a pair of posterior feet with curvilinear surfaces thereon for contact with condylar surfaces of the respective medial and lateral condyles, the end plate also having a posterior projection proximate to the elbow joint and having a convex curvilinear surface for contact with trochlear groove surfaces in an intercondylar region of the femur.

3. The surgical jig as in claim 1, wherein the jig is a tibial jig having a main medial block and a front plate coupled to the main medial block at an elbow joint, the main medial block having at least one planar slot therein coinciding with a desired cut plane when the jig is installed onto a tibia, an end extension projecting from a superior posterior surface of the front plate, the end extension having pairs of medial and lateral posterior feet with downward projections, the main medial block having a concave extension on an interior side of the elbow joint for contact with a side surface of the tibia, the downward projections of the posterior feet having underside curvilinear surfaces for contact with the medial and lateral condyles of the tibia at a position anterior to the tibial spine.

4. The surgical jig as in claim 1, wherein the set of rotational transformations with plane point transformations is repeated until changes in transformed images reduce below one or more specified thresholds.

* * * * *